United States Patent
Daum et al.

(10) Patent No.: US 7,962,210 B2
(45) Date of Patent: Jun. 14, 2011

(54) IMPLANTABLE MEDICAL DEVICE WITH VOICE RESPONDING AND RECORDING CAPACITY

(75) Inventors: Douglas R. Daum, Woodbury, MN (US); Qingsheng Zhu, Wexford, PA (US); Bruce H. KenKnight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 35 days.

(21) Appl. No.: 12/468,648

(22) Filed: May 19, 2009

(65) Prior Publication Data
US 2009/0228058 A1 Sep. 10, 2009

Related U.S. Application Data

(60) Division of application No. 11/071,984, filed on Mar. 4, 2005, now Pat. No. 7,551,962, which is a continuation of application No. 10/215,237, filed on Aug. 8, 2002, now Pat. No. 6,865,424, which is a continuation of application No. 09/473,466, filed on Dec. 28, 1999, now Pat. No. 6,453,201, which is a continuation-in-part of application No. 09/421,746, filed on Oct. 20, 1999, now abandoned.

(51) Int. Cl.
*A61N 1/362* (2006.01)
(52) U.S. Cl. ........... 607/32; 607/2; 607/4; 607/5; 607/9; 607/17; 607/18; 607/27; 607/28; 607/30; 607/60; 600/508; 600/513; 600/528; 600/586
(58) Field of Classification Search .................. 607/1–2, 607/4–5, 9, 17, 18, 27–28, 30, 32, 59–60; 600/508, 513, 528, 586
See application file for complete search history.

(56) References Cited

U.S. PATENT DOCUMENTS

| | | | |
|---|---|---|---|
| 3,586,261 A | 6/1971 | Palme |
| 3,623,486 A | 11/1971 | Berkovits |
| 3,631,860 A | 1/1972 | Lopin |
| 3,738,369 A | 6/1973 | Adams et al. |
| 3,799,147 A | 3/1974 | Adolph et al. |
| 4,066,086 A | 1/1978 | Alferness et al. |
| 4,094,308 A | 6/1978 | Cormier |
| 4,208,008 A | 6/1980 | Smith |
| 4,289,141 A | 9/1981 | Cormier |
| 4,432,360 A | 2/1984 | Mumford et al. |

(Continued)

FOREIGN PATENT DOCUMENTS

EP 0491649 6/1992

(Continued)

OTHER PUBLICATIONS

"U.S. Appl. No. 09/473,466 Non-Final Office Action mailed Nov. 7, 2001", 8 pgs.

(Continued)

*Primary Examiner* — Carl H Layno
*Assistant Examiner* — Deborah Malamud
(74) *Attorney, Agent, or Firm* — Schwegman, Lundberg & Woessner, P.A.

(57) ABSTRACT

An implantable medical device such as a cardiac pacemaker or implantable cardioverter/defibrillator with the capability of receiving communications in the form of speech spoken by the patient. An acoustic transducer is incorporated within the device which along with associated filtering circuitry enables the voice communication to be used to affect the operation of the device or recorded for later playback.

20 Claims, 1 Drawing Sheet

U.S. PATENT DOCUMENTS

| | | |
|---|---|---|
| 4,446,872 A | 5/1984 | Marsoner et al. |
| 4,548,204 A | 10/1985 | Groch et al. |
| 4,600,017 A | 7/1986 | Schroeppel |
| 4,628,939 A | 12/1986 | Little et al. |
| 4,649,930 A | 3/1987 | Groch et al. |
| 4,651,740 A | 3/1987 | Schroeppel |
| 4,721,114 A | 1/1988 | DuFault et al. |
| 4,725,956 A | 2/1988 | Jenkins |
| 4,763,646 A | 8/1988 | Lekholm |
| 4,793,361 A | 12/1988 | DuFault |
| 4,799,486 A | 1/1989 | DuFault |
| 4,799,493 A | 1/1989 | DuFault |
| 4,800,883 A | 1/1989 | Winstrom |
| 4,850,357 A | 7/1989 | Bach, Jr. |
| 4,872,459 A | 10/1989 | Pless et al. |
| 4,880,005 A | 11/1989 | Pless et al. |
| 4,905,706 A | 3/1990 | Duff et al. |
| 4,915,113 A | 4/1990 | Holman |
| 4,964,410 A | 10/1990 | Leahey et al. |
| 4,989,611 A | 2/1991 | Zanetti et al. |
| 4,998,531 A | 3/1991 | Bocchi et al. |
| 5,012,815 A | 5/1991 | Bennett, Jr. et al. |
| 5,040,212 A | 8/1991 | Bethards |
| 5,111,816 A | 5/1992 | Pless et al. |
| 5,129,392 A | 7/1992 | Bardy et al. |
| 5,159,932 A | 11/1992 | Zanetti et al. |
| 5,205,285 A | 4/1993 | Baker |
| 5,215,083 A | 6/1993 | Drane et al. |
| 5,247,945 A | 9/1993 | Heinze et al. |
| 5,271,392 A | 12/1993 | Ferek-Petric |
| 5,279,293 A | 1/1994 | Andersen et al. |
| 5,300,093 A | 4/1994 | Koestner et al. |
| 5,328,460 A | 7/1994 | Lord et al. |
| H1347 H | 8/1994 | Greeninger et al. |
| 5,334,222 A | 8/1994 | Salo et al. |
| 5,335,313 A | 8/1994 | Douglas |
| 5,365,932 A | 11/1994 | Greenhut |
| 5,427,112 A | 6/1995 | Noren et al. |
| 5,447,519 A | 9/1995 | Peterson |
| 5,450,525 A | 9/1995 | Russell et al. |
| 5,496,361 A | 3/1996 | Moberg et al. |
| 5,518,001 A | 5/1996 | Snell |
| 5,529,578 A | 6/1996 | Struble |
| 5,540,727 A | 7/1996 | Tockman et al. |
| 5,544,654 A | 8/1996 | Murphy et al. |
| 5,544,661 A | 8/1996 | Davis et al. |
| 5,554,177 A | 9/1996 | Kieval et al. |
| 5,584,868 A | 12/1996 | Salo et al. |
| 5,594,638 A | 1/1997 | Iliff |
| 5,607,460 A | 3/1997 | Kroll et al. |
| 5,615,380 A | 3/1997 | Hyatt |
| 5,633,910 A | 5/1997 | Cohen |
| 5,674,256 A | 10/1997 | Carlson |
| 5,685,317 A | 11/1997 | Sjostrom |
| 5,687,738 A | 11/1997 | Shapiro et al. |
| 5,697,375 A | 12/1997 | Hickey |
| 5,700,283 A | 12/1997 | Salo |
| 5,716,382 A | 2/1998 | Snell |
| 5,725,559 A | 3/1998 | Alt et al. |
| 5,749,900 A | 5/1998 | Schroeppel et al. |
| 5,749,907 A | 5/1998 | Mann |
| 5,749,908 A | 5/1998 | Snell |
| 5,752,976 A | 5/1998 | Duffin et al. |
| 5,774,357 A | 6/1998 | Hoffberg et al. |
| 5,792,195 A | 8/1998 | Carlson et al. |
| 5,792,204 A | 8/1998 | Snell |
| 5,792,205 A | 8/1998 | Alt et al. |
| 5,825,283 A | 10/1998 | Camhi |
| 5,836,987 A | 11/1998 | Baumann et al. |
| 5,843,142 A | 12/1998 | Sultan |
| 5,861,013 A | 1/1999 | Peck et al. |
| 5,867,386 A | 2/1999 | Hoffberg et al. |
| 5,875,108 A | 2/1999 | Hoffberg et al. |
| 5,888,187 A | 3/1999 | Jaeger et al. |
| 5,891,180 A | 4/1999 | Greeninger et al. |
| 5,899,928 A | 5/1999 | Sholder et al. |
| 5,901,246 A | 5/1999 | Hoffberg et al. |
| 5,903,454 A | 5/1999 | Hoffberg et al. |
| 5,920,477 A | 7/1999 | Hoffberg et al. |
| 5,921,938 A | 7/1999 | Aoyama et al. |
| 5,935,081 A | 8/1999 | Kadhiresan |
| 5,974,340 A | 10/1999 | Kadhiresan |
| 5,987,352 A | 11/1999 | Klein et al. |
| 5,991,661 A | 11/1999 | Park et al. |
| 6,006,132 A | 12/1999 | Tacker, Jr. et al. |
| 6,035,233 A | 3/2000 | Schroeppel et al. |
| 6,044,298 A | 3/2000 | Salo et al. |
| 6,044,299 A | 3/2000 | Nilsson |
| 6,045,513 A | 4/2000 | Stone et al. |
| 6,053,872 A | 4/2000 | Mohler |
| 6,058,329 A | 5/2000 | Salo et al. |
| 6,064,910 A | 5/2000 | Andersson et al. |
| 6,077,227 A | 6/2000 | Miesel et al. |
| 6,080,187 A | 6/2000 | Alt |
| 6,119,040 A | 9/2000 | Chirife |
| 6,139,505 A | 10/2000 | Murphy |
| 6,144,878 A | 11/2000 | Schroeppel et al. |
| 6,152,884 A | 11/2000 | Bjorgaas |
| 6,198,968 B1 | 3/2001 | Prutchi et al. |
| 6,254,544 B1 | 7/2001 | Hayashi |
| 6,256,536 B1 | 7/2001 | Kramer |
| 6,263,241 B1 | 7/2001 | Rosborough et al. |
| 6,264,611 B1 | 7/2001 | Ishikawa et al. |
| 6,272,377 B1 | 8/2001 | Sweeney et al. |
| 6,295,365 B1 | 9/2001 | Ota |
| 6,298,267 B1 | 10/2001 | Rosborough et al. |
| 6,298,269 B1 | 10/2001 | Sweeney |
| 6,312,378 B1 | 11/2001 | Bardy |
| 6,366,811 B1 | 4/2002 | Carlson |
| 6,368,283 B1 | 4/2002 | Xu et al. |
| 6,409,675 B1 | 6/2002 | Turcott |
| 6,415,033 B1 | 7/2002 | Halleck et al. |
| 6,438,421 B1 | 8/2002 | Stahmann et al. |
| 6,440,082 B1 | 8/2002 | Joo et al. |
| 6,453,201 B1 | 9/2002 | Daum et al. |
| 6,470,210 B1 | 10/2002 | Chen et al. |
| 6,477,406 B1 | 11/2002 | Turcott |
| 6,480,742 B2 | 11/2002 | Stahmann et al. |
| 6,527,729 B1 | 3/2003 | Turcott |
| 6,571,121 B2 | 5/2003 | Schroeppel et al. |
| 6,571,122 B2 | 5/2003 | Schroeppel et al. |
| 6,575,916 B2 | 6/2003 | Halleck et al. |
| 6,643,548 B1 | 11/2003 | Mai et al. |
| 6,650,940 B1 | 11/2003 | Zhu et al. |
| 6,665,564 B2 | 12/2003 | Lincoln et al. |
| 6,668,194 B2 | 12/2003 | VanHout |
| 6,678,547 B2 | 1/2004 | Carlson et al. |
| 6,792,308 B2 | 9/2004 | Corbucci |
| 6,795,732 B2 | 9/2004 | Stadler et al. |
| 6,810,287 B2 | 10/2004 | Zhu et al. |
| 6,824,519 B2 | 11/2004 | Narimatsu et al. |
| 6,830,548 B2 | 12/2004 | Bonnet et al. |
| 6,845,263 B2 | 1/2005 | Kawaguchi |
| 6,865,424 B2 | 3/2005 | Daum et al. |
| 6,907,289 B2 | 6/2005 | Stahmann et al. |
| 7,052,466 B2 | 5/2006 | Scheiner et al. |
| 7,113,825 B2 | 9/2006 | Pastore et al. |
| 7,115,096 B2 | 10/2006 | Siejko et al. |
| 7,123,962 B2 | 10/2006 | Siejko et al. |
| 7,551,962 B2 | 6/2009 | Daum et al. |
| 2002/0001390 A1 | 1/2002 | Kawaguchi |
| 2002/0016550 A1 | 2/2002 | Sweeney et al. |
| 2002/0035337 A1 | 3/2002 | Oka |
| 2002/0082509 A1 | 6/2002 | Vanderlinde et al. |
| 2002/0082645 A1 | 6/2002 | Sweeney |
| 2002/0107450 A1 | 8/2002 | Ogura |
| 2002/0120306 A1 | 8/2002 | Zhu et al. |
| 2002/0147401 A1 | 10/2002 | Oka |
| 2002/0151812 A1 | 10/2002 | Scheiner et al. |
| 2002/0151938 A1 | 10/2002 | Corbucci |
| 2002/0193847 A1 | 12/2002 | Daum et al. |
| 2003/0055352 A1 | 3/2003 | Hayek et al. |
| 2003/0060851 A1 | 3/2003 | Kramer et al. |
| 2003/0069608 A1 | 4/2003 | Sweeney |
| 2003/0072458 A1 | 4/2003 | Halleck et al. |
| 2003/0093002 A1 | 5/2003 | Kuo |
| 2003/0093003 A1 | 5/2003 | Watrous et al. |

| | | |
|---|---|---|
| 2003/0120159 A1 | 6/2003 | Mohler |
| 2003/0176896 A1 | 9/2003 | Lincoln et al. |
| 2003/0208240 A1 | 11/2003 | Pastore et al. |
| 2003/0216620 A1 | 11/2003 | Jain et al. |
| 2003/0229289 A1 | 12/2003 | Mohler |
| 2004/0024423 A1 | 2/2004 | Lincoln et al. |
| 2004/0039419 A1 | 2/2004 | Stickney et al. |
| 2004/0039420 A1 | 2/2004 | Jayne et al. |
| 2004/0064056 A1 | 4/2004 | Ogura |
| 2004/0078059 A1 | 4/2004 | Ding et al. |
| 2004/0078060 A1 | 4/2004 | Ding et al. |
| 2004/0106960 A1 | 6/2004 | Siejko et al. |
| 2004/0106961 A1 | 6/2004 | Siejko et al. |
| 2004/0127792 A1 | 7/2004 | Siejko et al. |
| 2004/0138572 A1 | 7/2004 | Thiagarajan |
| 2004/0167417 A1 | 8/2004 | Schulhauser et al. |
| 2004/0215264 A1 | 10/2004 | Van Bentem |
| 2004/0225332 A1 | 11/2004 | Gebhardt et al. |
| 2004/0236239 A1 | 11/2004 | Murray et al. |
| 2004/0254481 A1 | 12/2004 | Brodnick |
| 2004/0267147 A1 | 12/2004 | Sullivan |
| 2004/0267148 A1 | 12/2004 | Arand et al. |
| 2005/0027323 A1 | 2/2005 | Mulligan et al. |
| 2005/0033190 A1 | 2/2005 | Bauer |
| 2005/0137490 A1 | 6/2005 | Scheiner et al. |
| 2005/0240236 A1 | 10/2005 | Daum et al. |
| 2006/0282000 A1 | 12/2006 | Zhang et al. |

FOREIGN PATENT DOCUMENTS

| | | |
|---|---|---|
| EP | 0558353 | 9/1993 |
| WO | WO-97/43003 | 5/1996 |

OTHER PUBLICATIONS

"U.S. Appl. No. 09/473,466, Non-Final Office Action mailed Jun. 4, 2001", 9 pgs.

"U.S. Appl. No. 09/473,466, Notice of Allowance mailed Apr. 19, 2002", 5 pgs.

"U.S. Appl. No. 09/473,466, Response filed Feb. 7, 2002 to Non-Final Office Action mailed Nov. 7, 2001", 4 pgs.

"U.S. Appl. No. 09/473,466, Response filed Sep. 4, 2001 to Non-Final Office Action mailed Jun. 4, 2001", 7 pgs.

"U.S. Appl. No. 09/473,466, Supplemental Notice of Allowance mailed Jun. 26, 2002", 4 pgs.

"U.S. Appl. No. 09/833,229 Supplemental Response filed Sep. 29, 2005 to Advisory Action mailed Sep. 14, 2005", 10 pgs.

"U.S. Appl. No. 09/833,229, Advisory Action mailed Jul. 2, 2004", 3 pgs.

"U.S. Appl. No. 09/833,229, Final Office Action mailed Mar. 26, 2004", 12 pgs.

"U.S. Appl. No. 09/833,229, Final Office Action mailed May 5, 2005", 7 pgs.

"U.S. Appl. No. 09/833,229, Non-Final Office Action mailed Oct. 19, 2004", 10 pgs.

"U.S. Appl. No. 09/833,229, Notice of Allowance mailed Nov. 10, 2005", 4 pgs.

"U.S. Appl. No. 09/833,229, Response filed Jan. 18, 2005 to Non-Final Office Action mailed Oct. 19, 2004", 14 pgs.

"U.S. Appl. No. 09/833,229, Response filed Jan. 29, 2004 to Non-Final Office Action mailed Oct. 29, 2003", 16 pgs.

"U.S. Appl. No. 09/833,229, Response filed Apr. 3, 2003 to Non-Final Office Action Mailed Nov. 20, 2002", 13 pgs.

"U.S. Appl. No. 09/833,229, Response filed May 25, 2004 to Final Office Action mailed Mar. 26, 2004", 14 pgs.

"U.S. Appl. No. 09/833,229, Response filed Oct. 6, 2003 to Final Office Action mailed May 21, 2003", 15 pgs.

"U.S. Appl. No. 09/833,229, Advisory Action mailed Sep. 14, 2005", 3 pgs.

"U.S. Appl. No. 09/833,229, Final Office Action mailed May 21, 2003", 14 pgs.

"U.S. Appl. No. 09/833,229, Non-Final Office Action mailed Oct. 29, 2003", 13 pgs.

"U.S. Appl. No. 09/833,229, Non-Final Office Action mailed Nov. 20, 2002", 11 pgs.

"U.S. Appl. No. 09/833,229, Response filed Jun. 29, 2005 to Final Office Action mailed May 5, 2005", 12 pgs.

"U.S. Appl. No. 09/991,522 Non Final Office Action mailed Jul. 15, 2004", 17 pgs.

"U.S. Appl. No. 09/991,522 Notice of Allowance mailed Jan. 27, 2005", 5 pgs.

"U.S. Appl. No. 09/991,522 Response filed Oct. 15, 2004 to Non Final Office Action mailed Jul. 15, 2004", 9 pgs.

"U.S. Appl. No. 10/215,237, Final Office Action mailed Jul. 25, 2003", 7 pgs.

"U.S. Appl. No. 10/215,237, Non-Final Office Action Mailed Feb. 13, 2003", 10 pgs.

"U.S. Appl. No. 10/215,237, Non-Final Office Action mailed Dec. 17, 2003", 4 pgs.

"U.S. Appl. No. 10/215,237, Notice of Allowability mailed Sep. 28, 2004", 3 pgs.

"U.S. Appl. No. 10/215,237, Notice of Allowance mailed Oct. 14, 2004", 4 pgs.

"U.S. Appl. No. 10/215,237, Response filed Mar. 17, 2004 to Non-Final Office Action mailed Dec. 17, 2003", 6 pgs.

"U.S. Appl. No. 10/215,237, Response filed Nov. 25, 2003 to Final Office Action mailed Jul. 25, 2003", 8 pgs.

"Dream Hearing Aid Wish List", http://xp7.dejanews.com/getdoc.xp?recnu...db96q2&CONTEXT=862839689.31231&hitnum=0, Published by Deja News, Inc., (1995), pp. 1-2.

"Future Medical Reports Strong First Quarter Results", , http://www.growth.com/DMW/BISdmw.960517.html, Published by Berkshire Information Services, Inc., (May 17, 1996), pp. 1-3.

"Future Medical Technologies International Announces Launch of New Products", , http://www.growth.com/MENU/CVGR/PR/CVGR.950928.html, Published by Future Medical Technologies International, (May 5, 1997), 1 page.

"Kurzweil AI and Link Announces Availability of Kurzweil Clinical Reporter for Invasive Cardiology with Datalink", http://www.kurzweil.com/press/971703_card.html, Published by Kurzweil Applied Intelligence, Inc., (1996), pp. 1-4.

"Kurzweil Clinical Reporter", http://www.kurzweil.com/medical/kcr/faq.html, Published by Kurzweil Applied Intelligence, Inc., (1996), pp. 1-8.

"Voice Recognition Software in a Medical Office", http://www.voicerecognition.com/medical_office.html, Published by 21st Century Eloquence, Inc., (May 5, 1997), pp. 1-5.

Silvermint, Emanuel H, et al., "Medical Device Programmer/Recorder/Monitor With Voice Recognition", U.S. Appl. No. 09/306,605, filed May 6, 1999, 42 Pages.

"U.S. Appl. No. 09/833,229, Response filed Jul. 23, 2004 to Advisory Action mailed Jul. 2, 2004", 14 pgs.

"U.S. Appl. No. 09/833,229, Response filed Oct. 7, 2002 to Restriction Requirement mailed Sep. 11, 2002", 1 pg.

"U.S. Appl. No. 09/833,229, Restriction Requirement mailed Sep. 11, 2002", 4 pgs.

"U.S. Appl. No. 10/215,237, Response filed Jun. 13, 2003 to Non-Final Office Action mailed Feb. 13, 2003", 10 pgs.

"U.S. Appl. No. 10/215,237, Supplemental Notice of Allowability mailed May 5, 2004", 4 pgs.

"U.S. Appl. No. 11/037,276, Advisory Action mailed Oct. 29, 2008", 5 pgs.

"U.S. Appl. No. 11/037,276, Final Office Action mailed May 29, 2008", 8 pgs.

"U.S. Appl. No. 11/037,276, Final Office Action mailed Aug. 19, 2008", 9 pgs.

"U.S. Appl. No. 11/037,276, Non-Final Office Action mailed Feb. 20, 2009", 8 pgs.

"U.S. Appl. No. 11/037,276, Non-Final Office Action mailed Mar. 31, 2010", 4 pgs.

"U.S. Appl. No. 11/037,276, Non-Final Office Action mailed Aug. 21, 2009", 9 Pgs.

"U.S. Appl. No. 11/037,276, Non-Final Office Action mailed Oct. 31, 2007", 9 pgs.

"U.S. Appl. No. 11/037,276, Notice of Allowance mailed Sep. 30, 2010", 6 pgs.

"U.S. Appl. No. 11/037,276, Preliminary Amendment mailed Sep. 29, 2005", 8 pgs.

"U.S. Appl. No. 11/037,276, Response filed Jan. 31, 2008 to Non-Final Office Action mailed Oct. 31, 2007", 15 pgs.

"U.S. Appl. No. 11/037,276, Response filed May 20, 2009 to Non-Final Office Action mailed Feb. 20, 2009", 12 pgs.

"U.S. Appl. No. 11/037,276, Response filed Jun. 30, 2010 to Non-Final Office Action mailed Mar. 31, 2010", 8 pgs.

"U.S. Appl. No. 11/037,276, Response filed Jul. 28, 2008 to Final Office Action mailed May 29, 2008", 13 pgs.

"U.S. Appl. No. 11/037,276, Response filed Oct. 15, 2008 to Final Office Action mailed Aug. 19, 2008", 11 pgs.

"U.S. Appl. No. 11/037,276, Response filed Nov. 23, 2009 to Non-Final Office Action mailed Aug. 21, 2009", 13 pgs.

"U.S. Appl. No. 11/037,276, Response filed Dec. 19, 2008 to Advisory Action mailed Oct. 29, 2008", 11 pgs.

"U.S. Appl. No. 11/071,984, Final Office Action mailed Aug. 10, 2007", 18 pgs.

"U.S. Appl. No. 11/071,984, Final Office Action mailed Nov. 28, 2008", 13 pgs.

"U.S. Appl. No. 11/071,984, Non-Final Office Action mailed Feb. 22, 2007", 16 pgs.

"U.S. Appl. No. 11/071,984, Non-Final Office Action mailed Jun. 6, 2008", 14 pgs.

"U.S. Appl. No. 11/071,984, Notice of Allowance mailed Feb. 18, 2009", 6 pgs.

"U.S. Appl. No. 11/071,984, Preliminary Amendment mailed Jun. 28, 2005", 7 pgs.

"U.S. Appl. No. 11/071,984, Response filed Jan. 21, 2009 to Final Office Action mailed Nov. 28, 2008", 10 pgs.

"U.S. Appl. No. 11/071,984, Response filed Mar. 11, 2008 to Restriction Requirement mailed Jan. 22, 2008", 7 pgs.

"U.S. Appl. No. 11/071,984, Response filed May 22, 2007 to Non-Final Office Action mailed Feb. 22, 2007", 13 pgs.

"U.S. Appl. No. 11/071,984, Response filed Sep. 8, 2008 to Non-Final Office Action mailed Jun. 6, 2008", 11 pgs.

"U.S. Appl. No. 11/071,984, Response filed Oct. 30, 2007 to Final Office Action mailed Aug. 10, 2007", 15 pgs.

"U.S. Appl. No. 11/071,984, Restriction Requirement mailed Jan. 22, 2008", 7 pgs.

"Guidant Products", http://ww.guidant.com/products/, (Nov. 2000), 3 pgs.

Daum, Douglas R., "Implantable Medical Device With Voice Responding and Recording Capacity", U.S. Appl. No. 09/421,746, filed Oct. 20, 1999, 13 pgs.

Dyjach, John A, et al., "Method for Exclusion of Ectopic Events From Heart Rate Variability Metrics", U.S. Appl. No. 10/728,124, filed Dec. 4, 2003, 21 pgs.

Dyjach, John A., "Trended Measurement of Cardiac Resynchronization Therapy", U.S. Appl. No. 10/730,760, filed Dec. 8, 2003, 54 pgs.

IMPLANTABLE MEDICAL DEVICE WITH VOICE RESPONDING AND RECORDING CAPACITY

CROSS-REFERENCE TO RELATED APPLICATIONS

This patent application is a divisional of U.S. patent application Ser. No. 11/071,984, filed on Mar. 4, 2005, issued on Jun. 23, 2009 as U.S. Pat. No. 7,551,962, which is a continuation of U.S. patent application Ser. No. 10/215,237, filed on Aug. 8, 2002, issued on Mar. 8, 2005 as U.S. Pat. No. 6,865,424, which is a continuation of U.S. patent application Ser. No. 09/473,466, filed on Dec. 28, 1999, now issued on Sep. 17, 2002 as U.S. Pat. No. 6,453,201, which is a continuation-in-part of U.S. patent application Ser. No. 09/421,746, filed on Oct. 20, 1999, now abandoned, which is incorporated herein by reference.

FIELD OF THE INVENTION

This invention pertains to implantable medical devices and to methods and systems for operating same. In particular, the invention relates to means for communicating with such devices.

BACKGROUND

Modern pacemakers typically have the capability to communicate data via a radio-frequency link with an external programming device. Such data is transmitted to the pacemaker in order to program its mode of operation as well as define other operating parameters. Data transmitted from the pacemaker can be used to verify the operating parameters as well as relay information regarding the condition of both the pacemaker and the patient. Pacemaker patients are monitored at regular intervals as part of routine patient care and to check the condition of the device. Among the data which may typically be telemetered from the pacemaker are its programming parameters and an electrogram representing the electrical activity of the heart as sensed by the pacemaker. Pacemakers have also been developed which monitor certain parameters over time while the device is functioning in the patient. Data representing these parameters can be stored in memory for later retrieval using an external programmer.

SUMMARY OF THE INVENTION

It would be desirable in certain situations to be able to communicate with an implantable medical device such as a pacemaker without the need for an external programming device or any kind of equipment such as a radio transmitter/receiver. This would enable a patient, for example, to alter the operation of the device by such communication at any time or place as the need arises. Furthermore, the data recording capabilities of the implantable medical device could be activated by the patient whenever subjective symptoms are noted. The recorded data could then be retrieved later and analyzed for correlation with the symptoms experienced by the patient.

Accordingly, in one embodiment, the present invention is an implantable medical device, such as a cardiac pacemaker or implantable cardioverter/defibrillator, having incorporated therein a system enabling voice communication with the device so that the device responds to voice commands. The system includes an acoustic transducer and processing circuitry for sensing a patient's voice and deriving messages from words spoken by the patient, which messages may then alter the operation of the device. When a patient in whom the device is implanted speaks, the vibrating chords of the larynx cause acoustical energy to be radiated into the thorax where the acoustic transducer converts the energy into electrical audio signals. The audio signals can be analyzed with speech recognition circuitry to recognize certain words that correspond to system messages which are then employed to affect the operation of the device. In certain embodiments of the device, the patient's spoken commands can be used to alter the operating mode of a pacemaker, change operating parameters, or initiate recording of physiological data for later retrieval. Such recorded data can include, for example, electrograms, recordings of the patient's voice, heart sounds, respiratory patterns, or indications of physical activity.

In another embodiment, the invention is an implantable medical device, such as a cardiac pacemaker or implantable cardioverter/defibrillator, having incorporated therein a system enabling voice recording by the device, with the voice recording activated by either an external or internal signal. In the case of externally activated voice recording, the external signal may be, e.g., a voice, tactile, or magnetic signal imparted to the device by the patient or physician. An internal signal may be generated by the device upon sensing a particular physiological condition via its sensing channels, where the particular condition would typically be defined as one where it would be useful to have the subjective impressions of the patient while the condition is present, such as during an arrhythmic episode.

DESCRIPTION OF THE INVENTION

Figure 1:
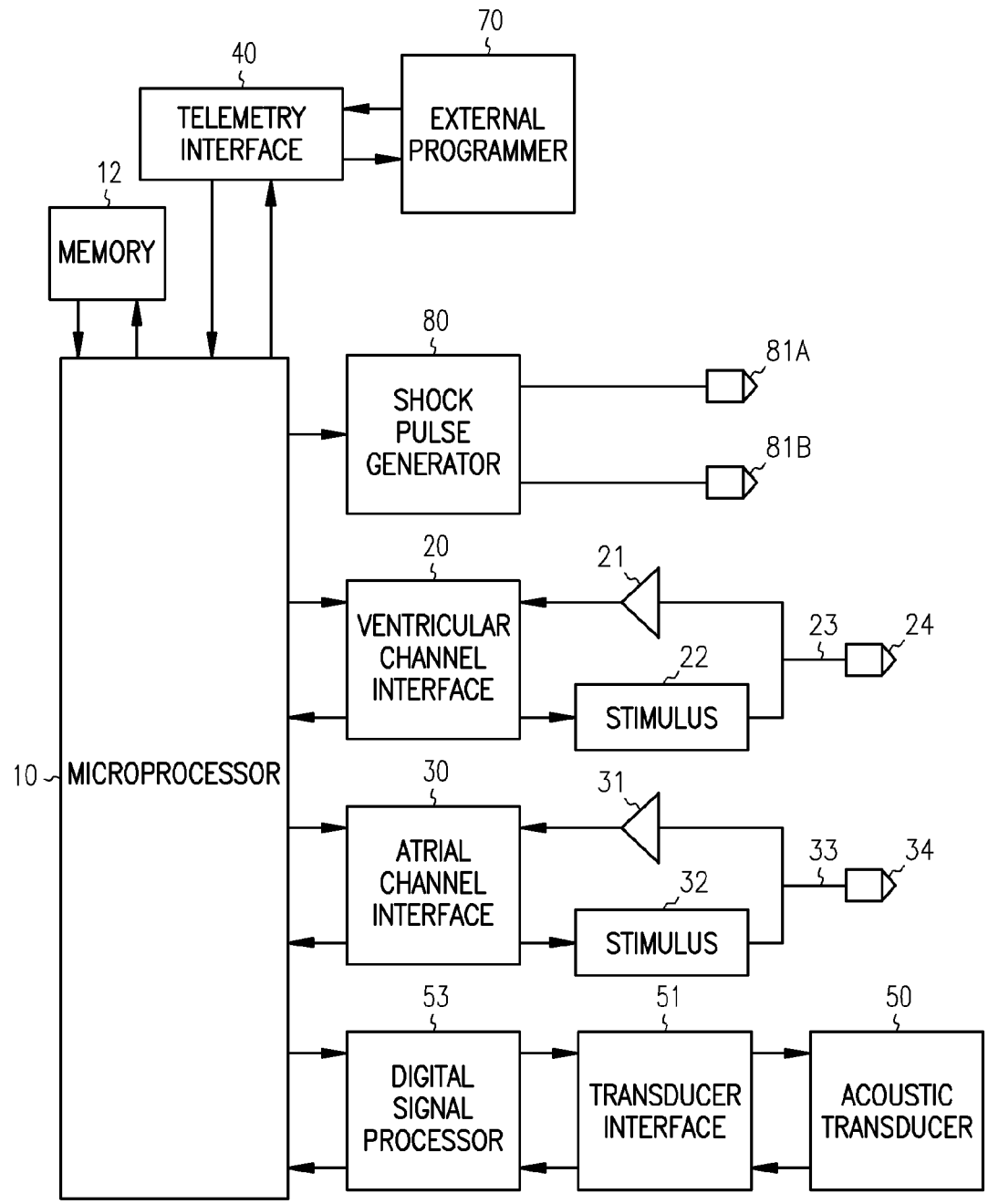
FIG. 1 is a system diagram of an implantable medical device incorporating the invention.

This application hereby incorporates by reference U.S. patent application Ser. No. 09/306,605, filed on May 6, 1999, now abandoned, in its entirety.

In the description that follows, a microprocessor-based pacemaker will be referred to as incorporating the present invention. It should be appreciated, however, the invention could also be incorporated into a pacemaker controlled by custom logic circuitry either in addition to or instead of a programmed microprocessor. The term "circuitry" as used herein should therefore be taken to mean either custom circuitry or a microprocessor executing programmed instructions contained in a processor-readable storage medium along with associated circuit elements.

FIG. 1 shows a system diagram of an implantable medical device, in this case is a microprocessor-based pacemaker with defibrillation and/or antitachycardia pacing capability, that incorporates the present invention. A microprocessor 10 communicates with a system memory 12 via a bidirectional system bus. Memory 12 may typically comprise a ROM for program storage and a RAM for data storage. The overall operation of the device is controlled by a system program running from the memory 12. The microprocessor also has a port for communicating with the telemetry interface 40 which in turn receives programming data from and transmits telemetry data to an external programmer 70 by a radio link. The pacemaker has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The channel interface includes sampling circuitry and an analog-to-digital converter for digitizing sensing signal outputs from the sensing amplifiers and registers which can be written to by the microprocessor in order to control pacing. A shock pulse generator 80 can also be interfaced to the microprocessor for delivering cardioversion or defibrillation pulses to the heart via a separate pair of electrodes 81*a* and 81*b*. Power for the device is provided by a battery.

An acoustic transducer 50 communicates with the microprocessor via a transducer interface 51. The transducer 50 may be an accelerometer or other piezo-resistive device capable of transducing acoustical energy from the patient's body into electrical signals. When the implantable medical device is implanted into a patient, the transducer 50 is capable of producing audio signals corresponding to the patient's voice, as acoustical energy produced by the patient's larynx is radiated into the thorax as well as into the air. The transducer interface 51 includes sampling circuitry for sampling the acoustic transducer output, an analog-to-digital converter for digitizing the samples, and circuitry for interfacing to a digital signal processor 53. Filtering of the transducer signals may also be performed by analog filters in the transducer interface 51 prior to digitization to reduce aliasing effects.

The digital signal processor interfaces to the microprocessor via the system bus and may incorporate speech recognition circuitry for extracting speech information from the digitized transducer signals. Such speech information may constitute specific groups of words that can be decoded into messages recognized by the system program. When such words are spoken by the patient, the messages cause the system program to alter the operation of the pacemaker. In different embodiments, a message derived from the speech information may cause the system program to alter the operation of the pacemaker by, for example, changing its operating mode, changing the operating parameters such as minimum heart rate, or causing the pacemaker to begin storage of sampled data in a storage medium such as the system memory 12.

Examples of such data storage include samples of the acoustic transducer output which therefore constitute recordings of the patient's voice or heart sounds, and samples of the sensing channel outputs thus forming a cardiac electrogram. Time stamps may also be applied to the recordings as they are made. Other types of data as recorded by other physiologic sensors incorporated into the device could also be recorded. The recordings can be later retrieved by transmission via the telemetry interface to an external programming device. Such recordings of physiological or voice data can then be correlated with symptoms experienced by the patient. This may be very useful to a treating physician in getting an accurate history of a cardiac event experienced by the patient, especially for those patients who are not able to adequately describe a cardiac event at much later clinical visit.

In another embodiment, voice recording is initiated upon receipt by the device of either an externally derived signal or an internal signal generated by the device itself. Examples of such external signals that could be used by particular embodiments are voice commands sensed and interpreted by the device as described above, operation of a magnetically-actuated reed switch with a magnet placed in proximity to the device (as is done to initiate a programming mode in conventional pacemakers), or manual operation of tactilely actuated switch by a user. In the case of a tactilely actuated switch, the tactile sensor actuating the switch could be, for example, a button placed on the outside of the implanted device which a user could access by pressing on the overlying skin, or a vibration sensor or accelerometer such as acoustic transducer 50 where acoustic signals generated by tactile stimuli applied to the device (e.g., by manually tapping) are interpreted as commands to activate voice recording. In another embodiment, voice recording could be activated when an internal signal is generated by the device when a condition corresponding to the onset of a physiologic or cardiac event is sensed by the device. In other embodiments, such externally and internally generated signals can be used to trigger other types of diagnostic storage including, e.g., recording of time stamps, cardiac electrograms, activity sensor outputs, and heart sound sensors, as well as to affect the operation of the device such as adjusting the pacing rate within predefined limits or turning on or off sensor dependent rate-responsive features.

In order to derive speech information from the acoustic transducer output corresponding to the patient's voice or to produce intelligible voice recordings for later playback, the acoustic transducer output must be sampled at some minimum rate. As both processor overhead and the memory requirements of the system increase with the sample rate, it is desirable to sample near this minimum rate. Although human hearing is capable of detecting audio frequencies up to 20 KHz, only a fraction of that bandwidth is needed to transmit normal speech. Phone lines in the U.S., for example, restrict the bandwidth of transmitted audio signals to below 4 KHz in order to prevent aliasing distortion when the signals are digitized. A level 0 digital signal used for transmitting a single voice channel over phone lines in the U.S., for example, is a pulse code modulated signal consisting of an analog voice signal sampled with 8 bits of quantization at a rate of 8000 samples per second. It has been found that intelligible speech can still result if an audio signal is bandlimited to at least as low as 2 KHz, which implies a minimum sampling rate of 4000 samples per second. At 4000 samples per second, a memory requirement of 80 Kilobytes would be needed for a 20 second recording. This figure can be reduced still further using various data compression techniques.

The implantable medical device as described thus enables a patient to affect the operation of the device with voice commands. In order to prevent inadvertent commands being issued to the device and restrict access to its voice control feature, the system could be programmed to ignore all messages derived from transduced speech unless a specific password is first spoken. Another password could be used to cause further speech to be ignored. Alternatively, the voice control feature could be rendered inactive until a specific input signal is received which could be, for example, operation of a reed switch by a magnetic field similar to the way external programmers typically communicate with pacemakers, or operation of a tactile sensor incorporated into the device.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method comprising:
   providing at least one of pacing therapy pulses, cardioversion shock pulses, or defibrillation shock pulses to a heart using an implantable medical device (IMD);
   producing digitized samples of acoustic energy received within a patient's body using the IMD, wherein the acoustic energy has sufficient bandwidth to allow recording of the patient's intelligible speech;

extracting speech information from the digitized samples;
decoding a voice command from the speech information;
recording, in response to the voice command, the digitized samples in a storage medium; and
transmitting the digitized samples to an external device.

2. The method of claim 1, wherein the recording includes storing the digitized samples using data compression.

3. The method of claim 1, wherein the acoustic energy further includes heart sounds.

4. The method of claim 1, wherein the acoustic energy further includes respiratory sounds.

5. The method of claim 4, including communicating stored samples of the respiratory sounds to the external device, wherein the external device is configured to correlate the stored samples of the respiratory sounds with patient symptoms.

6. The method of claim 1, wherein recording the digitized samples further includes activating the recording when a selected message is received through the acoustic energy.

7. The method of claim 1, wherein recording the digitized samples further includes activating the recording when detecting a physiologic event.

8. The method of claim 7, wherein the physiologic event includes cardiac arrhythmia.

9. The method of claim 1, including correlating the recorded digitized samples of the acoustic signal with patient symptoms.

10. The method of claim 9, including:
sensing electrical activity of the heart;
recording digitized samples of the sensed electrical activity; and
correlating the recorded samples of the sensed electrical activity signal with the recorded digitized samples of the acoustic signal and the patient symptoms.

11. The method of claim 9, including:
sensing physical activity of the patient;
recording digitized samples of the sensed physical activity; and
correlating the recorded samples of the patient physical activity signal with the recorded digitized samples of the acoustic signal and the patient symptoms.

12. The method of claim 1, including generating an internal signal in response to detection of a physiologic event, and wherein the recording the digitized samples includes activating the recording upon generation of the internal signal.

13. The method of claim 12, wherein generating an internal signal in response to detection of a physiologic event includes generating the internal signal in response to detection of a cardiac arrhythmia.

14. The method of claim 1, including changing a pacing rate in response to the voice command.

15. The method of claim 1, including changing activation of a sensor dependent rate responsive feature of the IMD in response to the voice command.

16. The method of claim 1, including changing an operating mode of the IMD in response to the voice command.

17. The method of claim 1, including activating anti-tachycardia pacing in response to the voice command.

18. The method of claim 1, including:
applying a timestamp to the recorded digitized samples; and
wherein the transmitting includes transmitting the digitized samples and timestamp to the external device.

19. The method of claim 1, including band-limiting the acoustic energy to two kilohertz (2 kHz) or less.

20. The method of claim 1, wherein recording the digitized samples includes recording the digitized samples in response to the voice command and a magnet being placed in proximity to the device.

* * * * *